(12) United States Patent
Spicer et al.

(10) Patent No.: US 6,531,600 B1
(45) Date of Patent: Mar. 11, 2003

(54) TREATMENT AND COMPOUNDS

(75) Inventors: Barbara Ann Spicer, Epsom (GB); Harry Smith, Epsom (GB); Harald Maschler, Nordstremmen (DE)

(73) Assignee: Beecham Group p.l.c., Brentford (GB)

( * ) Notice: Subject to any disclaimer, the term of this patent is extended or adjusted under 35 U.S.C. 154(b) by 0 days.

(21) Appl. No.: 09/708,338

(22) Filed: Nov. 8, 2000

Related U.S. Application Data

(62) Division of application No. 09/024,252, filed on Feb. 17, 1998, now Pat. No. 6,180,791, which is a division of application No. 08/477,157, filed on Jun. 7, 1995, now Pat. No. 5,734,051, which is a division of application No. 08/379,092, filed on Jan. 26, 1995, now abandoned, which is a continuation of application No. 08/208,765, filed on Mar. 9, 1993, now abandoned, which is a continuation of application No. 07/497,992, filed on Mar. 23, 1990, now abandoned.

(30) Foreign Application Priority Data

Mar. 23, 1989 (GB) .............................. 8906792

(51) Int. Cl.[7] .................. C07D 239/545; C07D 473/06; C07D 473/04; A61K 31/52; A61K 31/5377
(52) U.S. Cl. ..................................... 544/311
(58) Field of Search ....................... 544/311

(56) References Cited

U.S. PATENT DOCUMENTS

| 757,328 | A | 4/1904 | Massie et al. |
| 2,517,410 | A | 8/1950 | Papesch et al. |
| 4,120,947 | A | 10/1978 | Diamond |
| 4,450,163 | A | 5/1984 | Philippossian |
| 4,544,556 | A | 10/1985 | Fedi et al. |
| 4,593,095 | A | 6/1986 | Snyder et al. |
| 4,704,381 | A | 11/1987 | Schaumann et al. |
| 4,868,186 | A | 9/1989 | Franzone et al. |
| 4,879,300 | A | 11/1989 | Giordani et al. |

FOREIGN PATENT DOCUMENTS

EP           243192     * 10/1987

OTHER PUBLICATIONS

Klingler, "Syntheses von bronchospasmolytisch wirksamen β–Phenylathyl–aminoalkyl–xanthinen," *Arzneim.–Forsch/Drug Res.* 27(*I*): 4–14, (1977).

Cacace, et al., "Derivati della 8–ammino–teofillina," *Ann. Chim.* 47: 362–365, (1957).

Werner, et al., "Inhibition of the Synthesis of the TEM–Type β–Lactamase by Purine Derivatives,", *Arzneim.–Forsch/Drug Res. 31 (II)*: 2044–2048, (1981).

Blythin, et al., "Antiinflammatory Activity of Substituted 6–Hydroxyprimido[2,1–f]purine–2,4,8(1H,3H,9H)–tritones. Atypical Nonsteroidal Antiinflammatory Agents," *J. Med. Chem.* 29: 1099–1113, (1986).

Wells et al., "Inhibition of Seperated Forms of Cyclic Nucleotide Phosphodiesterase from Pig Coronary Arteries by 1,3–Disubstituted and 1,3,8–Trisubstituted Xanthines," *J. Med. Chem.* 24: 954–958, (1981).

Beavo, et al., "Effects of Xanthine Derivatives on Lipolysis and on Adenosine 3',5'–Monophosphate Phosphodiesterase Activity," *Molecular Pharmacology* 6(6): 597–603, (1970).

* cited by examiner

*Primary Examiner*—Mark L. Berch
(74) *Attorney, Agent, or Firm*—Dara L. Dinner; Stephen Venetianer; Charles M. Kinzig

(57) ABSTRACT

A method for the treatment of cerebrovascular disorders and/or disorders associated with cerebral senility and/or other disorders which method comprises the administration of an effective, non-toxic amount of a compound of formula (I):

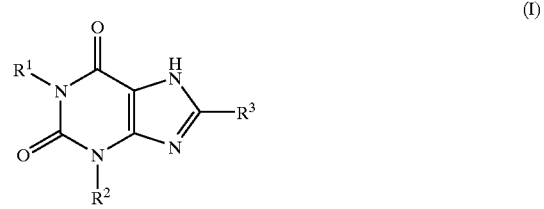

(I)

or if appropriate a pharmaceutically acceptable salt thereof, wherein $R^1$ and $R^2$ each independently represent alkyl or a moiety of formula (a):

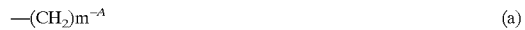

—(CH$_2$)$_m$—A                                      (a)

wherein m represents zero or an integer 1, 2 or 3; A represents a substituted or unsubstituted cyclic hydrocarbon radical; and $R^3$ represents a halogen atom, a nitro group, or a group $-NR^4R^5$ wherein $R^4$ and $R^5$ each independently represents hydrogen, alkyl or alkylcarbonyl or $R^4$ and $R^5$ together with the nitrogen to which they are attached forming an optionally substituted, heterocyclic group; certain novel compounds falling within formula (I) and compositions comprising such compounds.

7 Claims, No Drawings

TREATMENT AND COMPOUNDS

This application is a divisional of U.S. Ser. No. 09/024,252, filed Feb. 17, 1998 (now U.S. Pat. No. 6,180791) which is a divisional of U.S. Ser. No. 08/477,157, filed Jun. 7, 1995 (U.S. Pat. No. 5,734,051), which is a divisional of U.S. Ser. No. 08/379,092, filed Jan. 26, 1995 (abandoned), which is a continuation of U.S. Ser. No. 08/028,765, filed Mar. 9, 1993 (abandoned) which is a continuation of U.S. Ser. No. 07/497,992 filed Mar. 23, 1990 (abandoned).

The present invention relates to a novel method of treatment and to certain novel compounds having pharmacological activity, to a process for the preparation of such compounds, to pharmaceutical compositions containing such compounds and to the use of such compounds and compositions in medicine.

Molecular Pharmacology, Volume 6, No. 6, 1970, p. 597–603 discloses 1,3-dimethyl-8-nitro-xanthine. This compound is disclosed as having lipolytic activity.

Annalen der Chemie, 47, 362–365 (1957) discloses 1, 3-dimethyl-8-amino-xanthine and a process by which it may be prepared. No pharmacological utility is disclosed for this compound.

Drug Res. 27 (1) Nr. 19, 1977, pages 4–14, Van K. H. Klingler discloses certain 1, 3-dimethyl-8-substituted xanthines as intermediates solely in the synthesis of phenylethyl aminoalkyl xanthines.

Drug Res. 31 (11), Nr. 12, 1981, R. G. Werner et al, pages 2044–2048 discloses certain 1, 3-dimethyl-8-substituted xanthines. No pharmacological activity is disclosed for these compounds.

It has now been discovered that certain 8-substituted xanthines have a protective effect against the consequences of cerebral metabolic inhibition. The said compounds improve data acquisition or retrieval following transient forebrain ischaemia and are therefore useful in the treatment of cerebral vascular and neuronal degenerative disorders associated with learning, memory and cognitive dysfunctions including cerebral senility, multi-infarct dementia, senile dementia of the Alzheimer type, age associated memory impairment and certain disorders associated with Parkinson's disease.

These compounds are also indicated to have neuroprotectant activity. They are therefore useful in the prophylaxis of disorders associated with neuronal degeneration resulting form ischaemic events, including cerebral ischaemia due to cardiac arrest, stroke and also after cerebral ischaemic events such as those resulting from surgery and or during childbirth. In addition treatment with the compound is indicated to be of benefit for the treatment of functional disorders resulting from disturbed brain function following ischaemia.

These compounds are also active in increasing the oxygen tension in ischaemic skeletal muscle. This property results in an increase in the nutritional blood flow through ischaemic skeletal muscle which in turn indicates that the compounds of the invention are of potential use as agents for the treatment of peripheral vascular disease such as intermittent claudication.

These compounds also act as phosphodiesterase inhibitors and elevate cyclic AMP levels and are therefore of potential use in the treatment of proliferative skin disease in human or non-human mammals.

These compounds are also indicated to have bronchodilator activity and thus to be of potential use in the treatment of disorders of the respiratory tract, such as reversible airways obstruction and asthma.

It has now also surprisingly been discovered that these compounds are good inhibitors of induced blood eosinophilia and that they are therefore potentially useful in the treatment and/or prophylaxis of disorders associated with increased numbers of eosinophils, such as asthma, and allergic disorders associated with atopy, such as urticaria, eczema and rhinitis.

Certain of the novel compounds are also indicated to possess useful adenosine Al antagonist activity.

Finally the present compounds also show good metabolic stability.

Accordingly, the invention provides a method for the treatment of cerebrovascular disorders and/or disorders associated with cerebral senility and/or prophylaxis of disorders associated with neuronal degeneration resulting from ischaemic events and/or peripheral vascular disease and/or proliferative skin disease and/or for disorders of the respiratory tract and/or the treatment or prophylaxis of disorders associated with increased numbers of eosinophils and allergic disorders associated with atopy, which method comprises the administration of an effective, non-toxic amount of a compound of formula (I):

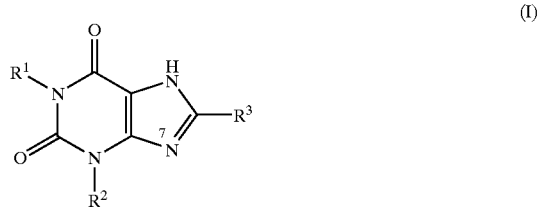

(I)

or if appropriate a pharmaceutically acceptable salt thereof, wherein $R^1$ and $R^2$ each independently represent alkyl or a moiety of formula (a):

$$-(CH_2)_m-A$$  (a)

wherein
 m represents zero or an integer 1, 2 or 3;
 A represents a substituted or unsubstituted cyclic hydrocarbon radical; and
 $R^3$ represents a halogen atom, a nitro group, or a group $-NR^4R^5$ wherein $R^4$ and $R^5$ each independently represents hydrogen, alkyl or alkylcarbonyl or $R^4$ and $R^5$ together with the nitrogen to which they are attached form an optionally substituted, heterocyclic group; to a human or non-human mammal in need thereof.

In another aspect, the invention provides the use of a compound of formula (I), or if appropriate a pharmaceutically acceptable salt thereof, for the manufacture of a medicament for the treatment of cerebrovascular disorders and/or disorders associated with cerebral senility and/or prophylaxis of disorders associated with neuronal degeneration resulting from ischaemic events and/or peripheral vascular disease and/or proliferative skin diseases and/or disorders of the respiratory tract and/or the treatment or prophylaxis of disorders associated with increased numbers of eosinophils and allergic disorders associated with atopy.

The present invention also provides a pharmaceutical composition comprising a compound of formula (I) or if appropriate a pharmaceutically acceptable salt thereof and a pharmaceutically acceptable carrier therefor.

The present invention also provides a pharmaceutical composition comprising a compound of formula (I), or if appropriate a pharmaceutically acceptable salt thereof, providing that in the compound of formula (I) when $R^1$ and $R^2$ both represent methyl then $R^3$ is not a nitro group, and a pharmaceutically acceptable carrier therefor.

In a further aspect the invention provides a compound of formula (I), or if appropriate a pharmaceutically acceptable salt thereof, providing that in the compound of formula (I) when $R^1$ and $R^2$ both represent methyl then $R^3$ is not a nitro group, for use as an active therapeutic substance.

The invention also provides a compound of formula (I), or if appropriate a pharmaceutically acceptable salt thereof, providing that in the compound of formula (I) when $R^1$ and $R^2$ both represent methyl then $R^3$ is not a nitro group, for use in the treatment of cerebrovascular disorders and/or disorders associated with cerebral senility and/or prophylaxis of disorders associated with neuronal degeneration resulting from ischaemic events and/or peripheral vascular disease and/or proliferative skin diseases and/or disorders of the respiratory tract and/or the treatment or prophylaxis of disorders associated with increased numbers of eosinophils and allergic disorders associated with atopy.

As indicated above, certain of the compounds of formula (I) are novel and form a further aspect of the present invention.

Accordingly, the invention also provides a compound of formula (IA):

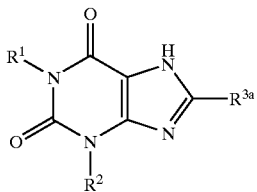

(IA)

or if appropriate a pharmaceutically acceptable salt thereof, wherein $R^1$ and $R^2$ each independently represent alkyl or a moiety of formula (a):

$$-(CH_2)_m-A \quad (a)$$

wherein m represents zero or an integer 1, 2 or 3, A represents a substituted or unsubstituted cyclic hydrocarbon radical, providing that when $R^1$ represents methyl then $R^2$ is not methyl; and $R^{3a}$ represents a halogen atom, a nitro group, or a group $-NR^4R^5$ wherein $R^4$ and $R^5$ each independently represent hydrogen, alkyl or alkylcarbonyl or $R^4$ and $R^5$ together with the nitrogen to which they are attached form an optionally substituted heterocyclic group.

Suitably, $R^1$ represents a moiety of formula (a).
Suitably, $R^2$ represents a moiety of formula (a).
Preferably, $R^1$ and $R^2$ each independently represent a moiety of formula (a).
Suitably, A is unsubstituted. Favourably, A represents a substituted or unsubstituted $C_{3-8}$ cycloalkyl group, especially a $C_{3-6}$ cycloalkyl group.
In particular, A represents a substituted or, preferably, unsubstituted cyclopropyl, cyclobutyl, cyclopentyl or cyclohexyl group.
Favourably, A represents a cyclopropyl group or a cyclobutyl group.
Preferably, A represents a cyclopropyl group.
When $R^1$ or $R^2$ represents alkyl, a preferred alkyl group is an n-butyl group.

An example of $R^3$ or $R^{3a}$ includes a nitro group or a group $-NHR^4$ wherein $R^4$ represents hydrogen or alkylcarbonyl.

When $R^3$ or $R^{3a}$ represents a halogen atom it is suitably a bromine or a chlorine atom.

When either of $R^4$ or $R^5$ represents alkyl or alkylcarbonyl, it is preferred if the other of $R^4$ or $R^5$ represents hydrogen.

An example of an alkylcarbonyl group is an acetyl group.

Suitable heterocyclic groups include saturated or unsaturated heterocyclic groups having single or fused rings, each ring having 5 to 7 ring atoms which ring atoms optionally comprise up to two additional hetero atoms selected from O, N or S.

Favoured heterocyclic groups include rings comprising 5 to 7, especially 5 or 6 and preferably 6, ring atoms.

Favoured additional hetero atoms are O or N, especially O.

Favoured heterocyclic groups are saturated heterocyclic groups.

Favoured heterocyclic groups are single ring heterocyclic groups.

Favoured heterocyclic groups comprising 5 ring atoms include pyrrolidinyl groups.

Favoured heterocyclic groups comprising 6 ring atoms include piperidinyl or morpholinyl groups.

Suitably, $R^3$ represents amino.
Suitably, $R^{3a}$ represents amino
Suitably, m represents zero or the integer 1.
Favourably, m represents 1.

Suitable pharmaceutically acceptable salts are pharmaceutically acceptable base salts and pharmaceutically acceptable acid addition salts. Generally compounds of formula (I) wherein $R^3$ is nitro form base salts, suitable pharmaceutically acceptable base salts of the compound of formula (I) include 7-N base salts including metal salts, such as alkali metal salts for example sodium salts, or organic amine salts such as that provided with ethylenediamine.

Certain of the compounds of formula (I) wherein $R^3$ is amino form acid addition salts, suitable acid addition salts of the compounds of formula (I) are the acid addition salts including pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphate, α-keto glutarate, α-glycerophosphate and glucose-1-phosphate. Preferably the acid addition salt is a hydrochloride salt.

The pharmaceutically acceptable salts of the compounds of formula (I) are prepared using conventional procedures.

A suitable compound of formula (I) is a compound of formula (IA).

When used herein the term 'cyclic hydrocarbon radical' includes single ring and fused ring, cyclic hydrocarbons comprising up to 8 carbon atoms in each ring, suitably up to 6 carbon atoms, for example 3, 4, 5 or 6 carbon atoms.

Suitable optional substitutents for any cyclic hydrocarbon radical includes a $C_{1-6}$ alkyl group or a halogen atom.

When used herein the term 'alkyl' whether used alone or when used as part of another group (for example as in an alkylcarbonyl group) includes straight and branched chain alkyl groups, containing from 1 to 12 carbon atoms, suitably 1 to 6 carbon atoms, for example methyl, ethyl, propyl or butyl.

When used herein the expression 'proliferative skin diseases' means benign and malignant proliferative skin diseases which are characterized by accelerated cell division in the epidermis, dermis or appendages thereto, associated with incomplete tissue differentiation. Such diseases include:

psoriasis, atopic dermatitis, non=specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

The compounds of formula (I) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

The invention further provides a process for the preparation of a compound of formula (IA), which process comprises reacting a compound of formula (II):

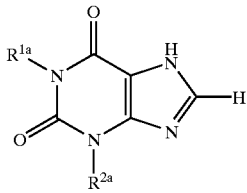

(II)

wherein $R^{1a}$ represents $R^1$, as defined in relation to formula (IA), or a group convertible to $R^1$ and $R^{2a}$ represents $R^2$, as defined in relation to formula (IA), or a group convertible thereto, with a reagent capable of substituting the C-8 hydrogen of the compound of formula (II) with a group $R^{3b}$ wherein $R^{3b}$ represents $R^{3a}$, as defined above in relation to formula (IA), or a group convertible thereto; and thereafter, if required carrying out one or more of the following optional steps:

(i) converting any group $R^{1a}$ to $R^1$ and/or $R^{2a}$ to $R^2$;

(ii) when $R^{3b}$ is not $R^{3a}$, converting $R^{3b}$ to $R^{3a}$;

(iii) converting a compound of formula (IA) into a further compound of formula (IA);

(IV) converting a compound of formula (IA) into a pharmaceutically acceptable salt.

For compounds of formula (IA) wherein $R^{3a}$ represents nitro, $R^{3b}$ preferably represents $R^{3a}$ i.e. nitro.

For compounds of formula (IA) wherein $R^{3a}$ represents other than nitro, $R^{3b}$ preferably represents a group convertible to $R^{3a}$.

One preferred group $R^{3b}$ is a nitro group which may then if required be converted to a group $R^{3a}$.

Suitable reagents for substituting the C-8 hydrogen of the compound of formula (II) with a group $R^{3b}$ are the appropriate conventional reagents.

The conditions of reaction for the substitution of the C-8 hydrogen of the compound of formula (II) will of course depend upon the particular reagent chosen, and in general the conditions used will be those which are conventional for the reagent used.

One particularly suitable reagent is a nitrating agent.

In one convenient form of the abovementioned process the compound of formula (II) is reacted with a suitable nitrating agent to provide a compound of formula (IA) wherein $R^{3a}$ represents a nitro group and then converting the nitro group into a halogen atom or a group of the abovedefined formula $-NR^{4a}R^{5a}$.

Accordingly, in one particular aspect the present invention provides a process for preparing a compound of formula (IA) which process comprises reacting a compound of the hereinbefore defined formula (II) with a nitrating agent, to provide a compound of formula (IA) wherein $R^{3a}$ represents a nitro group, and thereafter if required carrying out the following optional steps:

(i) converting any group $R^{1a}$ to $R^1$ and/or $R^{2a}$ to $R^2$;

(ii) converting the nitro group into another group $R^{3a}$;

(iii) converting a compound of formula (IA) into a pharmaceutically acceptable salt.

A compound of formula (II) may be prepared by the dehydrating cyclisation of a compound of formula (III):

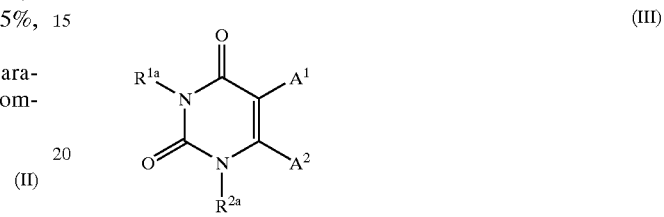

(III)

wherein $R^{1a}$ represents $R^1$, as defined in relation to formula (IA), or a group convertible to $R^1$ and $R^{2a}$ represents $R^2$, as defined in relation to formula (IA), or a group convertible thereto, $A^1$ represents —NO or —NH.CHO and $A^2$ represents —NH.CH$_3$ or –NH$_2$, providing that when $A^1$ is —NO then $A^2$ is —NH.CH$_3$ and when $A^1$ is —NH.CHO then $A^2$ is NH$_2$; and thereafter, if required, converting any group $R^{1a}$ to $R^1$ and/or $R^{2a}$ to $R^2$. The dehydrating cyclisation of a compound of formula (III) may be carried out under any suitable conditions. Favourably the conditions chosen are these wherein the water formed is removed from the reaction mixture, thus the reaction is generally carried out at an elevated temperature in the range of from 100° C. to 200° C., such as in the range of 180° C. to 190° C.

In one aspect of the process, especially when $A^1$ is —NO and $A^2$ is –NH.CH$_3$, the reaction is carried out in a solvent immiscible with water, such as toluene, at the reflux temperature of the solvent, the water being removed using a water-separator.

Suitable values for $R^{1a}$ and $R^{2a}$ include $R^1$ and $R^2$ respectively or nitrogen protecting groups such as benzyl groups.

When $R^{1a}$ or $R^{2a}$ represents other than $R^1$ or $R^2$ respectively, the abovementioned conversions of $R^{1a}$ into $R^1$ and $R^{2a}$ to $R^2$ may be carried out using the appropriate conventional procedure. For example when $R^{1a}$ (or $R^{2a}$) represents a nitrogen protecting group, such as a benzyl group, the protecting group may be removed using the appropriate conventional procedure, such as catalytic hydrogenation, and the resulting product reacted with a compound of formula (IV):

$$X-(CH_2)_m-A \qquad (IV)$$

wherein A and m are as defined in relation to formula (IA) and X represents a leaving group, such as halide, for example bromide or iodide.

The protection of any reactive group or atom, such as the xanthine nitrogen atom may be carried out at any appropriate stage in the aforementioned process. Suitable protecting groups include those used conventionally in the art for the particular group or atom being protected, for example suitable protecting groups for the xanthine nitrogen atoms are benzyl groups.

Protecting groups may be prepared and removed using the appropriate conventional procedure:

For example, N-benzyl protecting groups may be prepared by treating the appropriate compound of formula (II) with benzyl chloride in the presence of a base such as triethylamine. The N-benzyl protecting groups may be removed by catalytic hydrogenation over a suitable catalyst, such as palladium on activated charcoal, in a suitable solvent, such as ethanol conveniently at an elevated temperature, or by treatment with anhydrous aluminum chloride in dry benzene at ambient temperature.

A compound of formula (III) wherein $A^1$ represents —NH.CHO and $R^2$ represents —NH$_2$ may suitably be prepared from a 6-aminouracil of formula (A) according to the following reaction scheme:

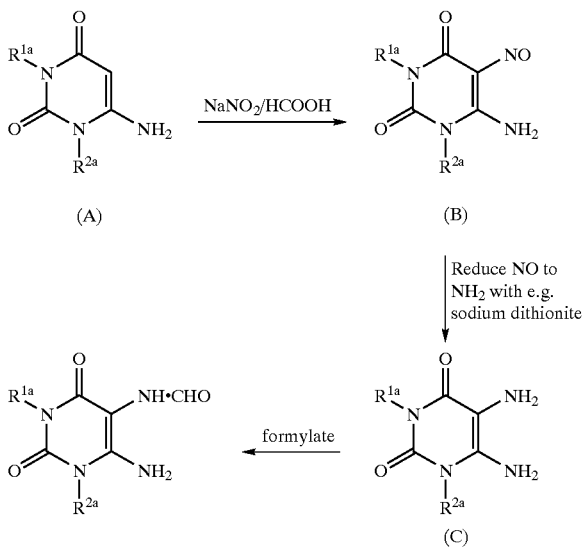

wherein $R^{1a}$ and $R^{2a}$ are as defined in relation to formula (II).

Suitably, the reaction conditions used in the above-mentioned reaction scheme are appropriate conventional conditions. In a preferred aspect of the process, the conversion of the 6-aminouracil (A), via (B) and (C), to the corresponding compound of formula (III) and the cyclisation of the compound of formula (III) to the compound of formula (II) are all carried out in-situ, suitably by using an analogous procedure to that of H. Bredereck and A. Edenhofer, Chem. Berichte 88, 1306–1312 (1955).

The 6-aminouracils of formula (A) may themselves be prepared by the method of V. Papesch and E. F. Schroder, J. Org. Chem., 16, 1879–90 (1951), or Yozo Ohtsuka, Bull. Chem. Soc. Jap., 1973, 46(2), 506–9.

A compound of formula (III) wherein $A^1$ represents —NO and $A^2$ represents -NH.CH$_3$ may conveniently be prepared from a 6-chlorouracil of formula (D), according to the following reaction scheme:

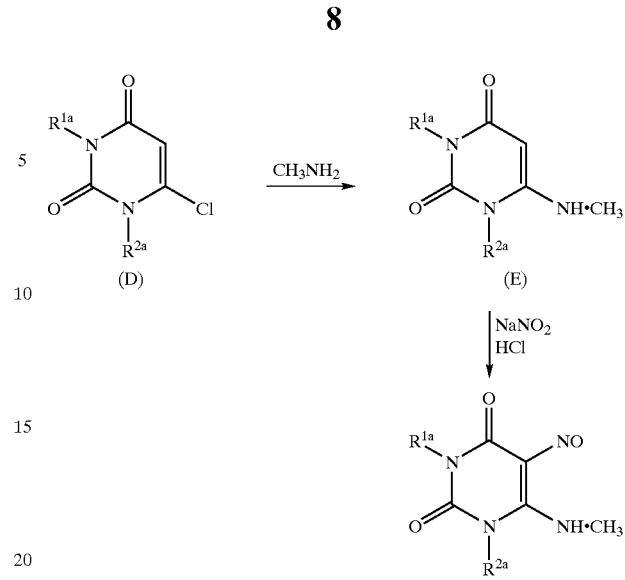

wherein $R^{1a}$ and $R^{2a}$ are as defined in relation to formula (II).

Suitably, the reaction conditions used in the last above mentioned scheme are the appropriate conventional conditions, for example those used in the method of H. Goldner, G. Dietz and E. Carstens, Liebigs Annalen der Chemie, 691, 142–158 (1965). The 6-chlorouracil of formula (D) may also be prepared according to the procedure of Dietz et al.

When $R^{3a}$ represent a nitro group, suitable conversions of the nitro group into another group $R^{3a}$ include the following:

(i) converting the nitro group into a halogen atom;
(ii) converting the nitro group into an amine group;
(iii) converting the nitro group into a halogen atom followed by conversion of the halogen atom into a group —NR$^{4b}$R$^{5b}$ wherein R$^{4b}$ and R$^{5b}$ together with the nitrogen atom to which they attached form an optionally substituted heterocyclic group; and
(iv) converting the nitro group into an amino group and thereafter aklylating and/or acylating the amino group to provide a group —NR$^{4c}$R$^{5c}$ wherein R$^{4c}$ represents hydrogen, alkyl or alkylcarbonyl and R$^{5c}$ represents alkyl or alkylcarbonyl.

A nitro group may be converted into a halogen atom by using any convenient halogenating agent.

One suitable halogenating agent is a hydrogen halide, suitably reacted in aqueous conditions for example by using concentration hydrochloric acid or concentrated hydrobromic acid at an elevated temperature, for example in the range of from 50 to 150° C.

A further suitable halogenating agent is a phosphorus oxyhalide, such as phosphorous oxychloride, which may be reacted in any suitable solvent, such as dimethyl-formaide, suitably at an elevated temperature for example in the range of from 50° C. to 150° C.

A nitro group may conveniently be converted into an amino group by conventional reduction methods for example by using tin powder and concentrated hydrochloric acid at ambient temperature or by using sodium dithionite in aqueous methanol at ambient temperature.

When $R^{3a}$ in the compound of formula (IA) represents a halogen atom it may be converted into a group –NR$^{4b}$R$^{5b}$ by reacting with a reagent of formula (III):

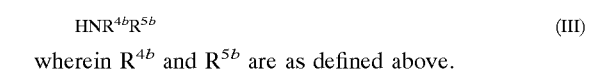

wherein $R^{4b}$ and $R^{5b}$ are as defined above.

The reaction between the compound of formula (IA) and the compound of formula (III) may be carried out in any suitable solvent, such as toluene, at any temperature providing a convenient rate of formation of the product, but suitably at an elevated temperature, such as in the range of from 50° to 180° C., at atmospheric or an elevated pressure.

Suitable alkylation methods for use in the abovementioned conversions include those used conventionally in the art, for example methods using halides, preferably iodides, in the presence of a base such as potassium carbonate in any convenient solvent for example acetonitrile or toluene.

Suitable acylation methods for use in the abovementioned conversions include those used conventionally in the art, thus an amino group may be converted into an alkylcarbonyl amino group by using an appropriate acylating agent, for example an amino group may be converted to an acetylamino group by using acetic anhydride at elevated temperature.

The compounds of formula (I) may be prepared according to the abovementioned methods or, as appropriate, by the methods of the abovementioned publications.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral, intravenous or intramuscular administration or through the respiratory tract. Preparations may be designed to give slow release of the active ingredient.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; perservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (I), or if appropriate a pharmaceutically acceptable salt thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulation that may be used for compounds of formula (I) or if appropriate a pharmaceutically acceptable salt thereof, are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound of formula (I), or if appropriate a pharmaceutically acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit does may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to about 1400 mg, such as from about 0.1 to about 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2mg/kg/day; and such therapy may extend for a number of weeks or months.

When used herein the term 'pharmaceutically acceptable' encompasses materials suitable for both human and veterinary use.

No toxicological effects have been established for the compounds of formula (I) in the above mentioned dosage ranges.

The following pharmacological data and examples illustrate the invention. The following preparations illustrate the preparation of intermediates to the novel compounds of formula (IA).

EXAMPLE 1

1,3-Di-n-butyl-8-nitro xanthine 1,3-Di-n-butylxanthine (73 g, 0.28 mol) was dissolved in acetic acid (120 ml) and then treated with concentrated nitric acid (49 g) at 87° C. After 1 hour, the mixture was cooled to 5° C., the resulting yellow precipitate filtered off and washed with water (50 ml). The yellow crystals were dissolved in dichloromethane and washed twice with water. The separate organic layer was then dried (anhydrous sodium sulphate) and concentrated to give a crystalline product, yield 73 g (86%), m.pt 168° C.

$^1$H NMR (CDCl$_3$/DMSO):

ppm: 0.93 (t, J=6.3 Hz, 6 H), 1.1–2.0 (m, 8 H), 3.8–4.25 (m, 4 H).

EXAMPLE 2

1,3-Di-cyclopropylmethyl-8-nitro xanthine 1,3-Di-cyclopropylmethyl xanthine (20 g, 0.76 mol) was dissolved in acetic acid (33 ml) and then treated with concentrated nitric acid (13.2 g). at 87° C. After 1 hour, the mixture was cooled to 5° C. and the resulting yellow precipitate filtered off. The yellow crystals were dissolved in dichloromethane and washed with water. The separated organic layer was then dried over anhydrous sodium sulphate and concentrated in vacuo. The product crystallized from the concentrate to yield a yellow crystalline product yield 12.2 g, (56.5%), m.pt. 207° C. (with decomposition).

$^1$H NMR (CDCl$_3$):

ppm: 0.35–0.7 (m, 8 H), 1.1–1.7 (m, 2 H), 3.95–4.2 (m, 4 H), 9.0–11.0 (br. exchanges with D$_2$O, 1 H).

The following compounds were prepared using an analogous procedure to that described in Example 1. The appropriate 1,3-di-cycloalkylmethyl xanthine substrates were prepared according to the procedures described herein in and in United Kingdom Patent Application No. 8826595.4.

TABLE 1

| Ex. No | R$^1$ | R$^2$ | R$^3$ | M.pt (° C.) | $^1$H NMR Spectrum: (CDCl$_3$ or CDCl$_3$/DMSO, ppm) |
|---|---|---|---|---|---|
| 3 | cyclobutylmethyl | cyclobutylmethyl | NO$_2$ | 220 | 1.7–2.2(m, 12H) 2.5–3.1(m, 2H) 4.1–4.3(m, 4H) |
| 4 | cyclopentylmethyl | cyclopentylmethyl | NO$_2$ | 148–150 | 1.1–2.0(m, 16H) 2.15–2.7(m, 2H) 4.15(d, J=7.7H$_z$, 4H) |
| 5 | cyclohexylmethyl | cyclohexylmethyl | NO$_2$ | 140 | 0.75–2.2(m, 22H) 3.7–4.1(m, 4H) |
| 6 | cyclopropylmethyl | cyclopropylmethyl | NO$_2$ | >250 | 0.7–1.4(m, 8H) 2.5–3.4(m, 2H) |

EXAMPLE 7

1,3-Di-n-butyl-8-amino xanthine hydrochloride 1,3-Di-n-butyl-8-nitro xanthine from Example 1 (8.5 g) was suspended in concentrated hydrochloric acid (85 ml) and then treated at room temperature with tin powder (14.5 g) in small portions. After stirring for 10 minutes the yellow colour of the suspension disappeared. Thereafter the precipitate was filtered off and recrystallised twice from ethanol. The product formed colourless crystals, yield 5.5 g (63%) m.pt>250° C.

$^1$H NMR (DMSO):

ppm: 0.90 (t, J=6.1 Hz, 6 H), 1.05–1.9 (m, 8 H), 3.65–4.15 (m, 4 H), 6.9 (br, exchanges with D$_2$O, 4 H).

EXAMPLE 8

1,3-Di-n-butyl-8-amino xanthine

Neutralisation of the hydrochloride from Example 6 with 1 N sodium hydroxide solution gave the 1,3-di-n-butyl-8-amino xanthine as a crystalline compound, yield 92%, m.pt. 89° C.

EXAMPLE 9

1,3-Di-cyclopropylmethyl-8-amino xanthine 1,3-Di-cyclopropylmethyl-8-nitro xanthine (4 g, 0.014 mol), suspended in 50 ml of concentrated hydrochloric acid, was treated with small portions of tin (8 g) at room temperature. The mixture was then stirred at room temperature for two hours.

The resulting precipitate was filtered off and crystallised from ethanol to give white crystals of the title product, yield 0.9 g (23%), m.pt. 281° C.

In an alternative procedure, using sodium dithionite as reducing agent (in methanol-water mixture). The yield was 36% (compare Example 13).

¹H NMR (CDCl₃):
ppm: 0.3–0.6 (m,8 H), 1.0–1.6 (m,2 H), 3.7–4.0 (m,4 H), 5.75 (br,2 H), 10.84 (br. exchanges with $D_2O$, 1 H).

EXAMPLES 10 to 12

The following compounds were prepared using an analogous procedure to that described above for the preparation of a compound of Example 7.

TABLE 2

| Ex. No | $R^1$ | $R^2$ | $R^3$ | M.pt (° C.) | ¹H NMR Spectrum: (CDCl₃ or CDCl₃/DMSO, ppm) |
|---|---|---|---|---|---|
| 10 | cyclopropylmethyl | cyclopropylmethyl | NH₂ | 124 (decomp) | 1.65–2.2(m, 12H) 2.5–3.1(m, 2H) 3.85–4.2(m, 4H) 6.5–8.5(br, 4H) |
| 11 | cyclopentylmethyl | cyclopentylmethyl | NH₂ | 300 | 1–1.9(m, 16H) 2.15–2.7(m, 2H) 3.65–4.0(m, 4H) 6.45(br, 2H) 11.20(br, 1H) |
| 12 | cyclohexylmethyl | cyclohexylmethyl | NH₂ | 300 | 0.7–2.2(m, 22H) 3.65–3.95(m, 4H) 6.51(s, 2H) 10–13(br, 1H) |

EXAMPLE 13

1,3-Di-cyclopropyl-8-amino xanthine 1,3-Di-cyclopropyl-8-nitro xanthine (0.4 g, 0.0014 mol) was dissolved in methanol (20 ml) and treated with a sodium dithionite solution in water (0.5 g in 5 ml) at room temperature with stirring. After stirring for three hours the solvent was removed in vacuo, the residue taken up with dichloromethane and extracted with water (40 ml).

After drying the organic layer over anhydrous sodium sulphate, the solvent was removed and the residue crystallised from ethanol, yield 0.06 g (17%), m.pt. >250² C.

¹H NMR (CDCl₃):
ppm: 0.6–1.4 (m, 8 H), 2.6–3.25 (m,2 H), 7.8 (s, 1 H), 12 (br. exchanges with $D_2O$, 1 H).

EXAMPLE 14

1,3-Di-n-butyl-8-acetamido xanthine 1.3-Di-n-butyl-8-amino xanthine (0.5 g), hydrochloride in toluene (30 ml) was stirred for 30 minutes with triethylamine (0.16 g). After addition of acetic anhydride (0.32 g), the mixture was refluxed for 6 hours. The reaction mixture was extracted with water (4×30 ml), the organic layer separated and dried over anhydrous sodium sulphate. The solvent was then evaporated to yield the product, yield 0.1 g (20%), mpt. 180° C.

¹H NMR (CDCl₃):
ppm: 0.93 (t, J=6.4 Hz, 6 H), 1.1–1.9 (m, 8 H), 2.27 (s, 3 H), 4.01 (t, J=6.7 Hz), 8.9 (br, exchanges with $D_2O$, 1 H).

EXAMPLE 15

1,3-Di-n-butyl-8-chloro xanthine 1,3-Di-n-butyl-8-nitro xanthine (0.5 g, 0.0016 mol) was refluxed for 18 hours with concentrated hydrochloric acid (8 ml). The reaction mixture was extracted with dichloromethane (20 ml), the organic layer washed with water to neutrality and then dried over anhydrous sodium sulphate. The solvent was then removed by evaporation in vacuo and the residue was recrystallised from ethanol, to give the title compound, yield 0.38 g (73%), m.pt. 152° C.

¹H NMR (CDCl₃):
ppm: 0.97 (t, J=6.1 Hz, 6 H), 1.1–2.0 (m, 8 H), 4.11 (t, J=7 Hz, 4 H), 13.1 (br., exchanges with $D_2O$, 1 H).

EXAMPLE 16

1,3-Di-n-butyl-8-bromo xanthine 1,3Di-n-butyl-8-bromo xanthine was prepared from 1,3-di-n-butyl-8-nitro xanthine (0.5 g, 0.0016 mol) and concentrated hydrobromic acid (8 ml) using the procedure was described in Example 15. The title product was obtained after recrystallisation from ethanol, yield 0.4 g (91%), m.pt. 178° C.

¹H NMR (CDCl₃):
ppm: 0.97 (t, J=6.1 Hz, 6 H), 1.1–2.0 (m, 8 H), 4.11 (t, J=6.9 Hz, 4 H), 13.3 (br. exchanges with $D_2O$, 1 H).

EXAMPLE 17

1,3-Di-cyclopropylmethyl-8-chloro xanthine 1,3-Di-cyclopropylmethyl-8-nitro xanthine (6 g, 0.023 mol) was dissolved in dimethylformamide (20 ml) and reacted with phosphorus oxychloride (14 g), for 1 hour at 120° C. The mixture was then treated with water and stirred for 1 hour at room temperature. The precipitate was filtered off, dissolved in ethyl acetate, dried over anhydrous sodium sulphate and the solvent was removed in vacuo, yield 2.5 g (40%), m.pt. 220° C.

¹H NMR (CDCl₃):
ppm: 0.35–0.65 (m, 8 H), 1.05–1.65 (m, 2 H), 4.1 (d, J=7.1 Hz, 4 H), 13.4 (br. exchanges with $D_2O$, 1 H).

EXAMPLE 18

1,3-Di-cyclohexyl-8-chloro xanthine 1,3-Di-cyclohexyl-8-chloro xanthine was prepared from 1,3-di-cyclohexyl-8-nitro xanthine (2 g, 0.006 mol) and phosphorus oxychloride (3.9 g) in dimethylformamide (6 ml), using an analogous procedure to that described in Example 17. The product was obtained as a crystalline product after recrystallisation from ethyl acetate, m.pt., 135° C.

¹H NMR (CDCl₃):
ppm: 1.0–2.7 (m, 20 H), 4.3–5.0 (m, 2 H).

EXAMPLE 19

1,3-Di-n-butyl-8-piperidino xanthine 1,3-Di-n-butyl-8-bromo xanthine (2 g, 0.0029 mol) was dissolved in toluene (50 ml). After addition of piperidine (5 g, 0.0058 mol) the mixture was refluxed for 9 hours. The reaction mixture was then extracted with water (4×30 ml), the organic layer dried over anhydrous sodium sulphate and the solvent removed in vacuo. The residue was recrystallised from ethanol to give the title product, yield 0.4 g (20%), m.pt. 221° C.

¹NMR (CDCl₃):
ppm: 0.85–1.15 (m, 6 H), 1.15–2.1 (m, 14 H), 3.5–3.8 (m, 4 H), 11 (br. exchanges with $D_2O$, 1 H).

EXAMPLE 20

1,3-Di-cyclopropylmethyl-8-morpholino xanthine 1,3-Di-cyclopropylemthyl-8-morpholino xanthine was prepared from 1,3-di-cyclopropylmethyl-8-chloro-xanthine (0.3 g, 0.001 mol) and morpholine (0.2 g, 0.0022 mol) using an analogous procedure to that described in Example 19. The title product was obtained as a crystalline solid, m.pt. >250° C., yield 0.09 g (26%).

$^1$H NMR (CDCl$_3$):

ppm: 0.3–0.65 (m, 8 H), 1.0–1.7 (m, 2 H), 3.5–4.2 (m, 12 H), 11.4 (br. exchanges with D$_2$O, 1 H).

EXAMPLE 21

1,3-Di-n-butyl-8-pyrrolidinyl xanthine

The title compound was prepared from 1,3-di-n-butyl-8-bromo xanthine (1 g, 0.0029 ml) and pyrrolidine (0.041 g, 0.0057 mol) using an analogous procedure to that described in Example 19. The title product was obtained as a crystalline solid, m.pt >250 C.

$^1$H NMR (CDCl$_3$):

ppm: 0.097 (t, J=6.3 Hz, 6 H), 1.1–2.25 (m, 12 H), 3.5–3.8 (m, 4 H), 3.8–4.2 (m, 4 H), 10.9 (br. exchanges with D$_2$O, 1 H).

EXAMPLE 22

1,3-Di-cyclopropylmethyl-8-pyrrolidinyl xanthine

The title compound was prepared from 1,3-di-cyclopropylmethyl-8-chloro xanthine (0.03 g, 0.0011 mol) and pyrrolidine (0.2 g, 0.0028 mol) using an analogous procedure to that described in Example 19. The title product was obtained as a crystalline solid, m.pt. >250° C.

$^1$H NMR (CDCl$_3$):

ppm: 0.3–065 (m, 8 H), 1.1–1.8 (m, 2 H), 1.9–2.2 (m, 4 H), 3.5–3.8 (m, 4 H), 3.8–4.1 (m, 4 H), 10.6 (br. exchanges with D$_2$O, 1 H).

EXAMPLE 23

1,3-Di-cyclopropylmethyl-8-piperidinyl xanthine

The title compound was prepared from 1,3-di-cyclopropylmethyl-8-bromo xanthine (1.2 g, 0.0037 mol) and piperidine (0.79 g, 0.009 mol) using an analogous procedure to that described in Example 19. The title product was obtained as a crystalline solid, m.pt. >250° C.

$^1$H NMR (CDCl$_3$):

ppm: 0.3–0.6 (m, 8 H), 1.05–1.55 (m, 2 H), 1.55–1.9, (m, 6 H), 3.45–3.8 (m, 4 H), 3.8–4.05 (m, 4 H), 13.3 (br., exchanges with D$_2$O, 1 H).

EXAMPLE 24

1,3-Di-cyclohexylmethyl-8-piperidinyl xanthine

The title compound was prepared from 1,3-di-cyclohexylmethyl-8-bromo xanthine (0.7 g, 0.0017 mol) and piperidine (0.28 g, 0.003 mol) using an analogous procedure to that described in Example 19. The title product was obtained as a crystalline solid, m.pt. 266° C.

$^1$H NMR (CDCl$_3$):

ppm: 0.75–2.2 (m, 28 H), 3.5–3.75 (m, 4 H), 3.75–4.05 (m, 4 H), 10.72 (br. exchanges with D$_2$O, 1 H).

EXAMPLE 25

1,3-Di-cyclohexylmethyl-8-bromo xanthine

The title compound was prepared from 1,3-di-cyclohexylmethyl 8-nitro xanthine (1 g, 0.0026 mol) and concentrated hydrobromic acid (40 ml, 48%) over 32 hours using an analogous procedure to that described in Example 15. The title product was obtained as a crystalline solid, m.pt. 247° C.

$^1$H NMR (CDCl$_3$):

ppm: 0.75–2.2 (m, 22 H), 3.89 (d, J=7.2 Hz, 4 H), 13.45 (br. exchanges with D$_2$O, 1 H).

EXAMPLE 26

1,3-Di-cyclohexyl-8-nitro xanthine

The title compound was prepared from 1,3-di-cyclohexyl xanthine (1.5 g, 0.0044 mol) concentrated nitric acid (0.56 g) and acetic acid (1.91 ml) using an analogous procedure to that described in Example 1. The title product was obtained as a crystalline solid, m.pt. >250° C.

$^1$H NMR (CDCl$_3$):

ppm: 0.8–2.7 (m, 20 H), 4–5 (m, 2 H).

Preparation 1

1,3-Di-cyclopropylmethyl xanthine 1,3-Di-cyclopropylmethyl xanthine was prepared using an analogous procedure to that described in Chem. Berichte 88, 1306–1312, 1955: 20.2 g (0.0855 mol) of 1,3-di-cyclopropylmethyl-6-amino-uracil was dissolved in 100 ml of formamide, then 5.9 g sodium nitrite was added and at 60° C. 13.4 ml formic acid was added slowly with stirring. After the colour had changed from yellow to violet, the mixture was heated up to 100° C. and 3.1 g of sodium dithionite (Na$_2$S$_2$O$_4$) was added in small portions.

Then the mixture was heated to 180–190° C. and held at this temperature for 30 minutes.

After cooling, the precipitate was sucked off, washed with 50 ml of water and recrystallised from toluene. Yield: 22.5 g, m.p. 203° C.

$^1$H NMR (CDCl$_3$):

ppm: 0.44–0.54 (8 H, q); 1.18–1.57 (2 H, m); 3.98–4.12 (4 H, 2 d); 7.81 (1 H, s); 12.8–13.2 (1 H, s, exch. with D$_2$O).

Preparation 2

1,3-Di-cyclobutylmethyl xanthine 1,3-Di-cyclobutylmethyl xanthine was prepared from 1,3-dicyclobutylmethyl-6-aminouracil using an analogous procedure to that described in Preparation 1. The title compound was isolated as a crystalline solid, m.p. 191° C.

$^1$H NMR (CDCl$_3$):

ppm: 1.6–2.3 (12 H, m); 2.4–3.2 (2 H, m); 4.16 (2 H, d, J=7.0 Hz); 4.21 (2 H, d, J=7.3 Hz); 7.76 (1 H, d, J=1.3 Hz, exch. with D$_2$O to give s) 12.7 (1 H, br.s, exch. with D$_2$O).

Preparation 3

1,3-Di-cyclopentylmethyl xanthine 1,3-Di-cyclopentylmethyl xanthine was prepared from 1,3-di-cyclopentylmethyl-6-aminouracil using an analogous procedure to that described in Preparation 1. The title compound was isolated as a crystalline solid, m.p. 208° C.

¹H NMR (CDCl₃):

ppm: 1.0–2.0 (16 H, m); 2.2–2.9 (2 H, m); 4.0–4.3 (4 H, m); 7.78 (1 H, d, J=1.2 Hz, exch. with D₂O to give s; 12.9 (1 H, br.s. exch. with D₂O).

Preparation 4

1,3-Di-cyclohexylmethyl xanthine 1,3-Di-cyclohexylmethyl xanthine was prepared from 1,3-di-cyclohexylmethyl-6-aminouracil using an analogous procedure to that described in Preparation 1. The title compound was isolated as a crystalline solid, m.p. 237° C.

¹H NMR (CDCl₃):

ppm: 0.8–2.2 (22 H, m); 3.85–4.15 (4 H, m (dd)); 7.73 (1 H, s); 13. 1 (1 H, br.s. exch. with D₂O).

Preparation 5

1,3-Di-cyclopropylmethyl-6-aminouracil 1,3-Di-cyclopropylmethyl-6-aminouracil was prepared using an analogous procedure to that described in J. Org. Chem. 16, 1879–1890, (1955):

22.6 g (0.138 mol) of the N,N'-dicyclopropylmethyl-urea (from Preparation 1) was treated with 44 ml (0.43 mol) of acetic anhydride and 14 g (0.165 mol) of cyanocetic-acid at 70° C. for 2 hours.

After cooling and the addition of 15 ml of water, 40 ml of 50% NaOH/water-solution was dropped slowly onto the mixture at 45° C. with stirring.

After stirring for 1 hour at room temperature, the strongly alkaline solution was separated and the oily residue washed carefully with 60 ml water.

The semi-solid residue was dissolved in 220 ml methanol and dropped into 1 litre of water with stirring. Thereby the product crystallised. Yield: 25.5 g, 78.5% approx., m.p. 85–95° C. (wax like).

Preparation 6

1,3-Di-cyclopentylmethyl-6-aminouracil 1,3-Di-cyclopentylmethyl-6-aminouracil was prepared from N,N'-di-cyclopentylmethyl urea using a procedure analogous to that described in Preparation 5. The title compound was isolated as a crystalline solid, m.p. 108° C.

¹H NMR (CDCl₃):

ppm: 1.0–2.6 (18 H, m); 3.86 (4 H, d J=7.4 Hz); 4.98 (3 H, m, 2 H exch. with D₂O).

Preparation 7

1,3-Di-cyclohexylmethyl-6-aminouracil 1,3-Di-cyclohexylmethyl-6-aminouracil was prepared from N,N'-di-cyclohexylmethyl urea using a procedure analogous to that described in Preparation 5. The title compound was isolated as a crystalline solid, m.p. 185° C.

Preparation 8

N,N'-Di-cyclopropylemthyl urea

N, N'-Di-cyclopropylmethyl urea, m.p. 124° C., was prepared using a procedure analogous to that described in J. Org. Chem. 16, 1879–1890, (1951):

68.2 g (0.634 mol) cyclopropylmethylamine-hydrochloride in 800 ml of water was treated with 25 g sodium hydroxide dissolved in 100 ml of water and the mixture cooled to −15° C.

Phosgene, 33 g was then slowly introduced through a capillary tube with stirring. Thereafter the mixture was stirred for 1 hour and, as necessary, after acidification with 0.1 N HCl, the product was extracted with dichloromethane.

After washing with water and drying over anhydrous sodium sulphate the product was obtained after evaporation of the solvent. Yield: 21 g, 40% approx.

From the aqueous phase, 20 g of the unreacted aduct (cyclopropylmethylamine-hydrochloride) can be obtained.

¹H NMR (CDCl₃):

ppm: 0.06–0.59 (8 H, m); 0.72–1.06 (2 H, m); 3.01–3.09 (4 H, d); 4.66 (1 H, br.s, exch. with D₂O).

Preparation 9

N,N'-Di-cyclobutylmethyl urea

N,N'-Di-cyclobutylmethyl urea was prepared from cyclobutylmethylamine using a procedure analogous to that described in Preparation 8. The title compound was isolated as a crystalline solid, m.p. 155° C.

¹H NMR (CDCl₃):

ppm: 1.4–2.8 (14 H, m); 3.0–3.3 (4 H, m); 4.59 (2 H, br. s, exch. with d₂O).

Preparation 10

N,N'-Di-cyclopentylmethyl urea

N,N'-Di-cyclopentylmethyl urea was prepared from cyclopentylmethylamine using a procedure analogous to that described in Preparation 4. The title compound was isolated as a crystalline solid, m.p. 150° C.

¹H NMR (CDCl₃):

ppm: 1.0–2.2 (18 H, m); 2.9–3.2 (4 H, m); 4.59 (2 H, br.s, exch. with D₂O).

Preparation 11

N,N'-Di-cyclohexylmethyl urea

N,N'-Di-cyclohexylmethyl urea was prepared from cyclo-hexylmethylamine using a procedure analogous to that described in Preparation 8. The title compound was isolated as a crystalline solid, m.p. 159° C.

PHARMACOLOGICAL DATA a) Inhibition of Cyclic AMP Phosphodiesterase

Procedure

The procedure used was that described by Arch, J. R. S. and Newsholme, E. A. in Biochem. J. 158, 603, (1976):

Erythrocytes were obtained from Na-citrate (16 mM; 0.1 ml/ml blood) anticoagulated blood by repeated centrifugation with removal of the buff coat and washing with an isotonic buffer (composition in mM; NaCl 13.7, KCl 4, $CaCl_2.2\ H_2O$ 1.8, $Na_2HPO_4.12\ H_2O$ 0.8, $NaH_2PO_4$ 0.2, $MgSO_4.7\ H_2O$ 0.7, Hepes 3.4; pH 7.4).

The phosphodiesterase was extracted by mixing the erythrocytes with 4 volumes of 7 mM phosphate buffer, pH7.4, followed by sonification (3×10 sec; 100 W) and then centrifuging for 30 min at 4200×g.

All supernatants were diluted in the extraction medium and assayed for phosphodiesterase activity within 6 hours of preparation, using the radiochemical procedure described in the above mentioned reference.

| Example No. | ki [μM] c-AMP phosphodiesterase (erythrocytes) |
|---|---|
| 1 | 17 |
| 2 | 15.9 |
| 3 | 6.1 |
| 4 | 4.8 |
| 5 | 5.4 |
| 7 | 1.3 |
| 9 | 1.6 |
| 10 | 0.53 |
| 11 | 0.57 |
| 13 | 14 |
| 17 | 15.1 |
| 18 | 23 |
| 19 | <100 |
| 20 | 11.5 |
| 22 | 29.7 |
| 23 | 55.9 |
| 25 | 7.9 | b) Induction of blood eosinophilia and the effects of drugs.
Animals

Male Charles River Sprague Dawley rats weight between 250 to 300 g were used.

The method used was a modification of that described by Laycock et al (Int. Arch. Appl. Immunol, (1986). 81, 363).

Sephadex G200, particle size 40 to 120 micron, was suspended in isotonic saline at 0.5 mg/ml, and stored for 48 h at 4° C. 1 ml of the suspension was given intravenously to rats on days 0,2 and 5. A control group received saline. The test compound was given before the Sephadex on each occasion, with a contact time expected to give maximum activity at the time of the Sephadex administration. Blood was taken from the tail vein of the rats on day 7 for the determination of total and differential leucocyte counts.

A control group of at least 6 animals was included each time a compound was evaluated. The control group received Sephadex and the vehicle without test compound. The results in the drug treated animals were compared with the control group. Alternatively, if the mean for the control group for any experiment was not statistically different from the mean of the sum of all of the controls groups, then the treated animal results for that experiment were compared with the mean of the sum of all the control groups.
Total and differential leucocyte counts 20 μl samples of blood, taken from the tail vein of the rats, were added to 10 ml of Isoton II and, within 30 min, Zaponin (3 drops) was added, to lyse the erythrocytes. Five minutes later the total cell count was determined using a Coulter Counter Model DN. Differential leucocyte counts were carried out by fixing and staining a blood smear on a microscopic slide with May-Grunwald and Giemsa stains. A minimum of 400 cells were counted on each slide.
Statistics Probability values were calculated using the Student's t test.
Results The effect of the test compound upon Sephadex induced eosinophilia in the rat is set out in Table 3. The test compound was given orally 30 minutes before each injection of Sephadex. The results indicate that the test compound inhibits the induced eosinophilia in a dose dependent manner.

TABLE 3

| Test Compound | Dose mg/kg (orally-30 mins) | % of Control Mean ± SEM (n = 12 or more) |
|---|---|---|
| Vehicle dosed control + sephadex i.v | — | 100 ± 7 |
| Negative control saline i.v. | — | 10 ± 0.9*** |
| Example 1 | 25.0 | 109 ± 6 |
| Example 7 | 25.0 | 91 ± 6 |
| Example 9 | 2.0 | 48 ± 7*** |
|  | 0.2 | 61 ± 8** |
| Example 10 | 5.0 | 47 ± 4*** |

Notes
**p < 0.01
***p < 0.001

What is claimed is:
1. A compound of Formula (III)

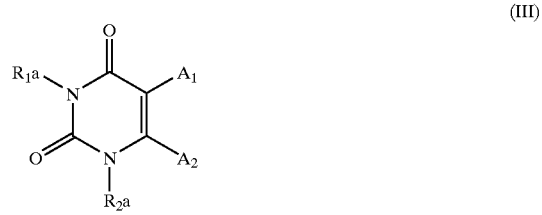

(III)

wherein
$R^{1a}$ and $R^{2a}$ each independently represent a moiety of formula (a):

—(CH$_2$)$_m$—A  (a)

wherein m represents an integer 1, 2 or 3; and
A represents a $C_{3-8}$ cycloalkyl group which may be unsubstituted or substituted with $C_{1-6}$ alkyl or halogen;
$A^1$ represents —NO or —NHCHO; and
$A^2$ represents —NHCH$_3$ or NH$_2$, provided that when $A^1$ is NO then $A^2$ is NHCH$_3$ and when $A^1$ is —NHCHO then $A^2$ is NH$_2$.

2. The compound according to claim 1 wherein A represents a substituted or unsubstituted cyclopropyl, cyclobutyl, cyclopentyl or cyclohexyl group.

3. The compound according to claim 2 wherein A represents a cyclopropyl or a cyclobutyl group.

4. The compound according to claim 3 wherein A represents a cyclopropyl group.

5. The compound according to claim 1 wherein $A^2$ represents an amino group.

6. The compound according to claim 1 wherein $A^2$ represents an NHCH$_3$ group.

7. The compound according to claim 1 wherein m is 1.

* * * * *